(12) United States Patent
Liu

(10) Patent No.: US 7,148,611 B1
(45) Date of Patent: Dec. 12, 2006

(54) MULTIPLE FUNCTION BULK ACOUSTIC WAVE LIQUID PROPERTY SENSOR

(75) Inventor: James Z T Liu, Hudson, NH (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/248,815

(22) Filed: Oct. 11, 2005

(51) Int. Cl.
*H01L 41/047* (2006.01)
(52) U.S. Cl. .................. 310/366; 310/338; 310/365
(58) Field of Classification Search ............ 310/366, 310/320, 321, 338, 365
See application file for complete search history.

(56) References Cited

U.S. PATENT DOCUMENTS

| | | | |
|---|---|---|---|
| 3,382,381 A * | 5/1968 | Horton | 310/320 |
| 5,117,146 A | 5/1992 | Martin et al. | 310/313 R |
| 5,155,708 A | 10/1992 | Bedi et al. | 367/152 |
| 5,208,162 A * | 5/1993 | Osborne et al. | 436/6 |
| 5,289,073 A | 2/1994 | Mariani | 310/313 D |
| 5,455,475 A * | 10/1995 | Josse et al. | 310/316.01 |
| 5,595,908 A * | 1/1997 | Fawcett et al. | 435/287.2 |
| 5,821,425 A | 10/1998 | Mariani et al. | 73/703 |
| 6,293,136 B1 | 9/2001 | Kim | 73/19.03 |
| 6,314,791 B1 | 11/2001 | Rapp et al. | 73/24.06 |
| 6,568,271 B1 | 5/2003 | Shah et al. | 73/599 |
| 6,571,638 B1 | 6/2003 | Hines et al. | 73/702 |
| 6,640,613 B1 | 11/2003 | Rapp et al. | 73/24.01 |
| 6,693,444 B1 | 2/2004 | Lin et al. | 324/698 |
| 6,781,388 B1 | 8/2004 | Wang et al. | 324/690 |
| 6,907,353 B1 * | 6/2005 | Sanchez Pina et al. | 702/30 |
| 2002/0113521 A1 | 8/2002 | Rapp et al. | 310/313 R |
| 2003/0057968 A1 | 3/2003 | Wang et al. | 324/690 |
| 2003/0076743 A1 | 4/2003 | Thompson et al. | 367/140 |
| 2003/0196477 A1 | 10/2003 | Auner et al. | 73/24.06 |
| 2004/0012399 A1 | 1/2004 | Lin et al. | 324/698 |
| 2005/0218757 A1* | 10/2005 | Yamaguchi et al. | 310/365 |

FOREIGN PATENT DOCUMENTS

KR    2005-68170    7/2005

OTHER PUBLICATIONS

J.R. Vig, *Dual-Mode Oscillators for Clocks and Sensors*, 1999 IEEE Ultrasonics Symposium, pp. 859-868.
J. Nieb, T. Hamacher, P.S. Lammers, E. Weber, P. Boeker, *A Miniaturized Thermal Desorption Unit for Chemical Sensing Below Odor Threshold*, 2003 Elsevier B.V.
J. ZT Liu, *Construction Optimization for Acoustic Wave Chemical Sensor Selectivity*, Champion Technologies Inc.

(Continued)

*Primary Examiner*—Darren Schuberg
*Assistant Examiner*—Derek Rosenau
(74) *Attorney, Agent, or Firm*—Richard H. Krukar; Luis M. Ortiz

(57) ABSTRACT

A multifunction sensor based on a bulk acoustic wave (BAW) device can be used to obtain measurements of a liquid's corrosivity, viscosity, and conductance. A front electrode and a back electrode can be used to excite vibrations in a piezoelectric substrate. Vibrations in the piezoelectric substrate cause an electrical signal that can be measured as a voltage differential between the front and back electrodes. The signal amplitude is an indication of the liquid's viscosity. The signal frequency is an indication of corrosivity because corrosion can change the sensor's fundamental frequency over time. A third electrode, a runner, can be placed near the front electrode. A voltage difference between the runner and the front electrode can cause a current to flow between them and through the liquid. The voltage difference and the current indicate the liquid's conductivity.

21 Claims, 4 Drawing Sheets

OTHER PUBLICATIONS

*QCM 100 Quartz Crystal Microbalance*, Stanford Research Systems, Inc.
*Crystal Etch Monitor CEM-1000 Data Sheet*, Transat Corp.
*Research Crystals-Quartz Crystals for Research Applications*, Maxtek, Inc.
*CHC-100/CHK-100/CHT-100 Crystal Holders*, Maxtek, Inc.
*TBN TAN*, OilChek, U.S. Oil Co. Inc.
M. Barnes, Noria Corporation, D. Wooton, Wooton Consulting, *Using Nuclear Magnetic Resonance to Track Additive Depletion*, Practicing Oil Analysis Magazine, Jul. 2005.

* cited by examiner

MULTIPLE FUNCTION BULK ACOUSTIC WAVE LIQUID PROPERTY SENSOR

TECHNICAL FIELD

Embodiments relate to the field of bulk acoustic wave devices. Embodiments also relate to measuring a liquids viscosity, corrosivity, and conductivity. Embodiments additionally relate to packaging multiple sensor functions in a single bulk acoustic wave device.

BACKGROUND

There are many applications in which certain physical properties of liquids are measured. Three of the physical properties are viscosity, corrosivity, and conductivity. Viscosity refers to the degree to which a fluid resists flow. For example, at room temperature molasses is far more viscous than water. Corrosivity refers to the degree to which a material reacts chemically with its environment. For example, a piece of iron rusts when exposed to the air. When a material corrodes, it generally gains or loses mass. Conductivity is the degree with which a material conducts electricity. Copper is more conductive than battery acid. Battery acid is more conductive than wood.

Bulk acoustic wave (SAW) sensors are electro acoustic devices that can be used to measure physical or chemical properties. A BAW sensor has a piezoelectric substrate and electrodes. A piezoelectric material is a material that expands or contracts in response to an electric field. Alternatively, squeezing or releasing a piezoelectric material can produce an electric field. Quartz, lithium niobate, lithium tantalite, and lithium iodate are four of the many piezoelectric materials known to those practiced in the arts of acoustic wave devices or piezoelectric materials.

Changing the electrode voltages on a BAW sensor can cause the substrate to expand or contract. Similarly, squeezing and releasing the substrate can cause a voltage difference to appear on the electrodes. Introducing an oscillating electric drive signal across the electrodes can cause an acoustic wave to develop in the substrate. In other words, the substrate vibrates. If the drive signal is suddenly removed, vibration continues. The continuing substrate vibrations cause an output signal to appear on the electrodes. The output signal has the same frequency content as the substrate vibrations and has an amplitude that is proportional to the amplitude of substrate vibrations.

An acoustic wave device also has at least one fundamental frequency. A fundamental frequency is the devices natural frequency. For example, a glass holding water has a fundamental frequency. Tapping the glass produces a sound corresponding to the glass' fundamental frequency. Changing the amount of water in the glass changes the fundamental frequency. Similarly, thickening, thinning, or similarly changing the mass of a BAW sensor can change the BAW sensor's fundamental frequencies.

Corrosion can change the thickness or mass of a BAW sensor. Oftentimes, an electrode includes a material that can corrode. For example, a measurement of the corrosivity of engine oil can be desired. A material that engine oil corrodes can be layered onto an electrode and then the electrode exposed to engine oil. The fundamental frequency of the BAW sensor then changes based on the corrosivity of the engine oil. As such, the corrosivity of a liquid can be measured because it corresponds to the change in a BAW sensor's fundamental frequency.

The viscosity of a liquid, such as the engine oil discussed above, can also be measured by a BAW sensor. The more viscous a liquid is, the more it resists flow. When exposed to a liquid, the amplitude of the BAW sensor vibrations is decreased because all fluids are viscous. The more viscous the liquid is, the smaller the BAW sensor vibrations are. Smaller amplitude BAW vibrations lead to smaller amplitude output signals at the electrodes. As such, the viscosity of a liquid can be measured because it corresponds to the amplitude of the electrode signal.

Liquids also have an electrical conductivity. Electrical conductivity can be measured by placing two electrodes into the liquid, causing a voltage difference between the electrodes, and then measuring the electric current passing from one electrode, through the liquid, and then through the other electrode. The liquid's conductivity can be found as a function of the number of ions per unit volume, electrode spacing, and electrode shape. Those practiced in the art of measuring physical properties know of this and other methods of using electrodes to measure conductivity.

Current technology supplies BAW sensors for measuring corrosivity and viscosity. AT and BT cut quartz crystals are used as piezoelectric substrates. Electrode materials are selected based on their chemical reactivity with a specified liquid. For example, engine oil corrosivity is interesting because the oil is corroding an engine. As such, an electrode material that corrodes similarly to engine components is chosen.

Current technology does not, however, supply an integrated sensor that for measures more than corrosivity and viscosity. In particular, it doesn't supply a sensor that can measure more physical propertied without incurring additional processing steps to construct the sensor. Aspects of the embodiments directly address the shortcoming of current technology by producing an additional structure on an integrated BAW sensor without requiring additional processing steps.

BRIEF SUMMARY

It is therefore an aspect of the embodiments that a piezoelectric substrate has a front side and a back side. A first conductor has a first contact on the back side and a front electrode on the front side. Electrical conductivity ensures that an electrical signal or voltage present on the first contact is present on the front electrode. A second conductor has a second contact on the back side and a back electrode on the back side. Electrical conductivity ensures that an electrical signal or voltage present on the second contact is present on the back electrode. A third conductor has a third contact on the back side and a runner on the front side. Electrical conductivity ensures that an electrical signal or voltage present on the third contact is present on the runner.

It is an additional aspect of the embodiments that the runner and the front electrode are separated by a small gap. The conductivity of the specified liquid can be measured by immersing the device, creating an electric field between the front electrode and the runner, and measuring the electrical current induced by the electric field that passes through the front electrode, specified liquid, and runner.

It is another aspect of the embodiments that the piezoelectric substrate can be made with any piezoelectric material, such as quartz. Quartz can be AT cut or BT cut.

It is also another aspect of the embodiments that the front electrode is chemically reactive with a specified liquid. As such, the front electrode can change in mass or geometry when exposed to the specified liquid. In certain embodiments, the front electrode can be coated with a material that is chemically reactive to the specified liquid. For example, a gold electrode is not chemically reactive with many liquids. Coating the gold electrode with aluminum, however, produces an electrode that is chemically reactive to many specified liquids. Furthermore, the electrode can be coated with a protein or similar organic substance that is chemically reactive with certain other organic or biological substances.

It is yet another aspect of the embodiments that acoustic vibrations can be created in the piezoelectric substrate by creating a varying electric field between the first contact and the second contact. Acoustic vibrations in the piezoelectric substrate can also be measured by measuring the signal between the first contact and the second contact. Amplitude variations can be used to find the specified liquid's viscosity. Changes in the signal's frequency can be used to measure corrosivity.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
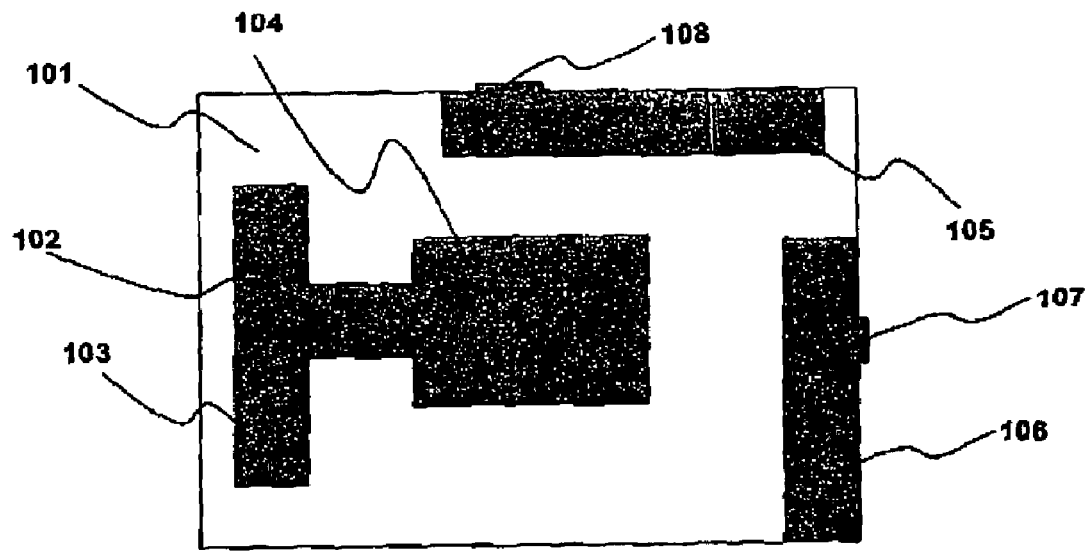
FIG. 1 illustrates the back side of a multifunction sensor in accordance with aspects of the embodiments.

FIG. 1 illustrates the back side of a multifunction sensor in accordance with aspects of the embodiments. A piezoelectric substrate 101 has a first conductor 108, second conductor 102, and a third conductor 107 attached to it. The first conductor 108 includes a first contact 105 and a front electrode (not shown). The second conductor 102 includes a second contact 103 and a back electrode 104. The third conductor 107 includes a third contact 106 and a runner (not shown).

Figure 2:
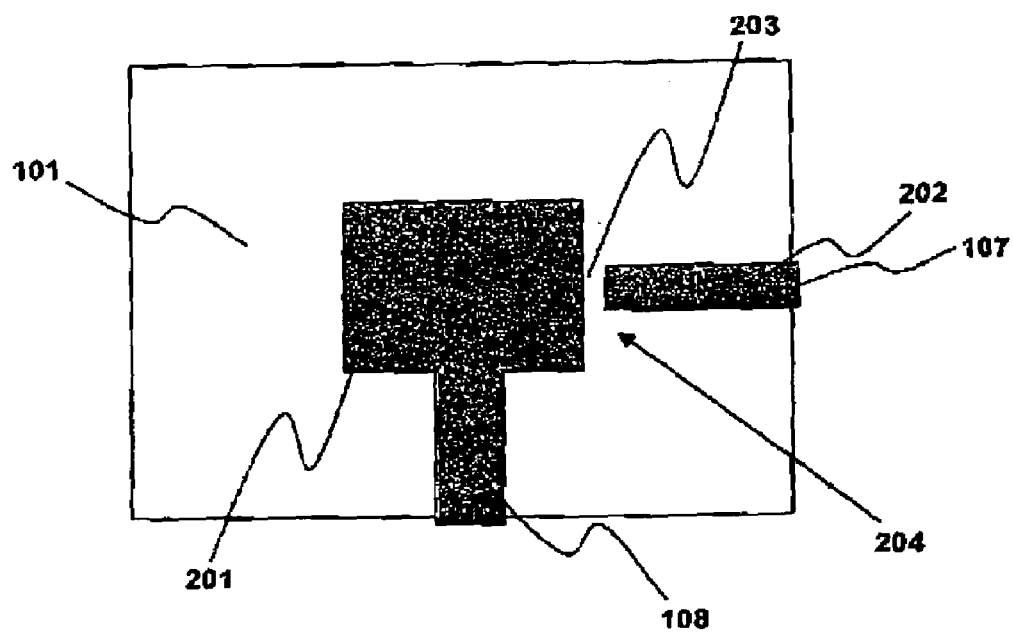
FIG. 2 illustrates the front side of a multifunction sensor in accordance with aspects of the embodiments.

FIG. 2 illustrates the front side of a multifunction sensor in accordance with aspects of the embodiments. The device illustrated in FIG. 2 is the device illustrated in FIG. 1 with the exception that a front side view is presented. The elements that were not shown attached to the piezoelectric substrate 101 in FIG. 1 are shown here attached to the front side of the piezoelectric substrate 101. The runner 202 is part of the third conductor 107. The front electrode 201 is part of the first conductor 108. A gap 203 between the front electrode 201 and the runner 202 can be used for measuring the conductivity of a liquid as discussed above. As such, the gap 203, front electrode 201, and runner 202 form a conductivity measuring element 204.

Figure 3:
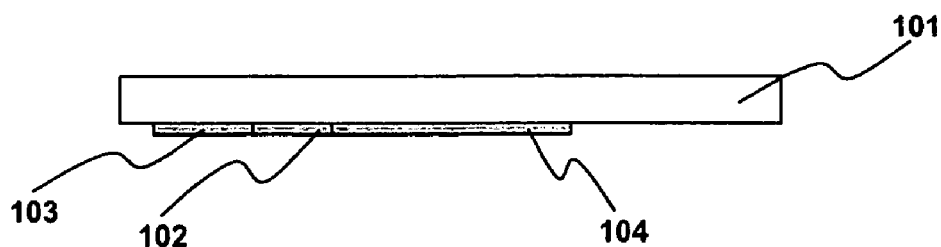
FIG. 3 illustrates a second conductor in accordance with aspects of the embodiments.

FIG. 3 illustrates a second conductor 102 in accordance with aspects of the embodiments. FIG. 3, which is not to scale, is a side view of the device illustrated in FIG. 1 and FIG. 2 without the first conductor or third conductor. The second conductor 102 is attached to the back side of the piezoelectric substrate 101 and includes the second contact 103 and back electrode 104.

Figure 4:
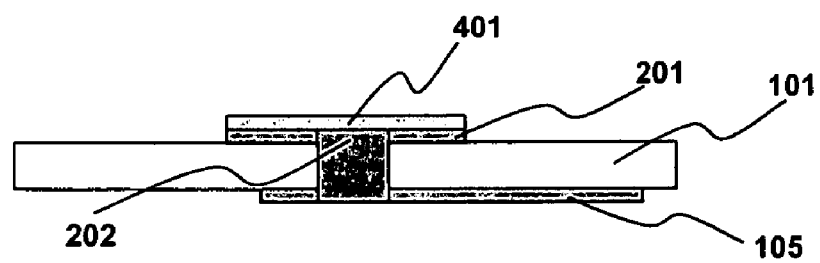
FIG. 4 illustrates a first conductor in accordance with aspects of some embodiments.

FIG. 4 illustrates a first conductor 108 in accordance with aspects of some embodiments. FIG. 4, which is not to scale, is a side view of a device similar to that illustrated in FIG. 1 and FIG. 2 without the second conductor or third conductor. The first conductor 108 is attached to both sides of the piezoelectric substrate 101. On the back side, the first conductor 108 has the first contact 105. On the front side, the first conductor 108 has the front electrode 201. Here, however, an additional layer 401 of material has been attached to the front electrode 201. In some embodiments, the additional layer 401 can be used because it is chemically reactive to a specified liquid.

Figure 5:
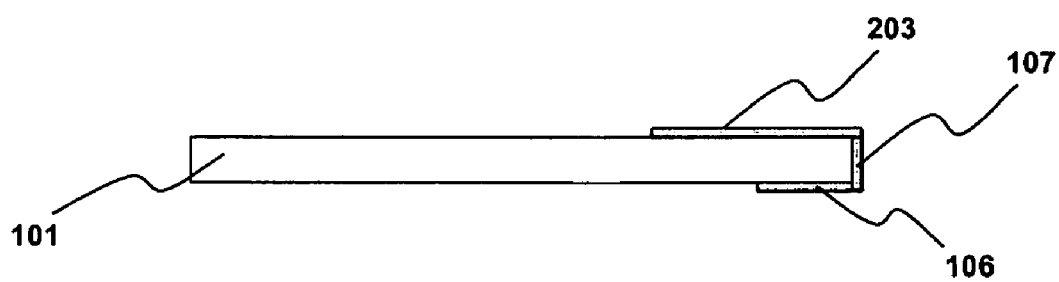
FIG. 5 illustrates a third conductor in accordance with aspects of the embodiments.

FIG. 5 illustrates a third conductor in accordance with aspects of the embodiments. FIG. 5, which is not to scale, is a side view of the device illustrated in FIG. 1 and FIG. 2 without the first conductor or second conductor. The third conductor 107 is attached to both sides of the piezoelectric substrate 101. On the back side, the third conductor 107 has the third contact 106 and on the front side the third conductor 107 has the runner 202.

Figure 6:
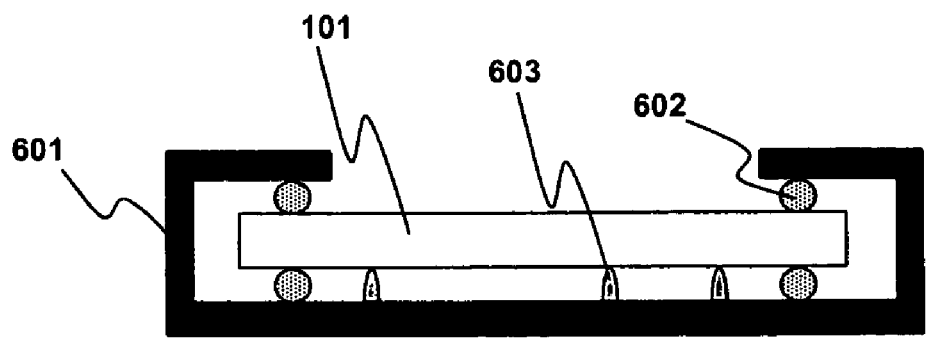
FIG. 6 illustrates a multifunction sensor in a housing in accordance with aspects of certain embodiments.

FIG. 6 illustrates a multifunction sensor 604 in a housing 601 in accordance with aspects of certain embodiments. A sealing element 602, such as an o-ring or silicone bead, is used to hold the multifunction sensor 604 in the housing 601 and as a seal. Pins 603 are used to establish electrical connections to the contacts of the multifunction sensor. There can be additional circuitry, such as an analog electronics module or a micro controller, within the housing 101.

Figure 7:
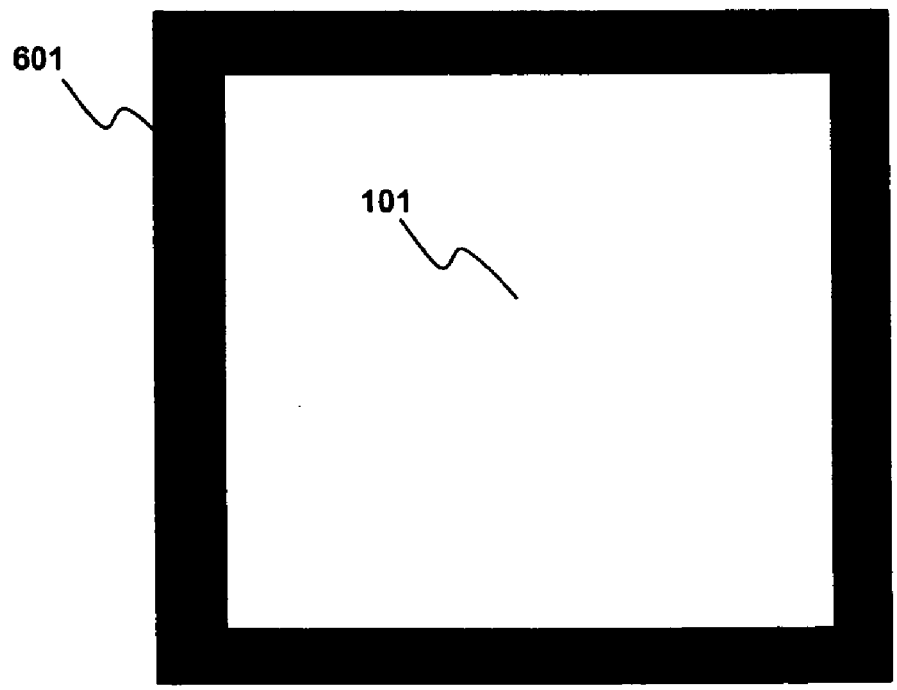
FIG. 7 illustrates a top view of a multifunction sensor in a housing in accordance with aspects of certain embodiments.

FIG. 7 illustrates a top view of a multifunction sensor 604 in a housing 601 in accordance with aspects of certain embodiments. FIG. 7 is simply another view of the device illustrated in FIG. 6 and is presented for clarity.

Figure 8:
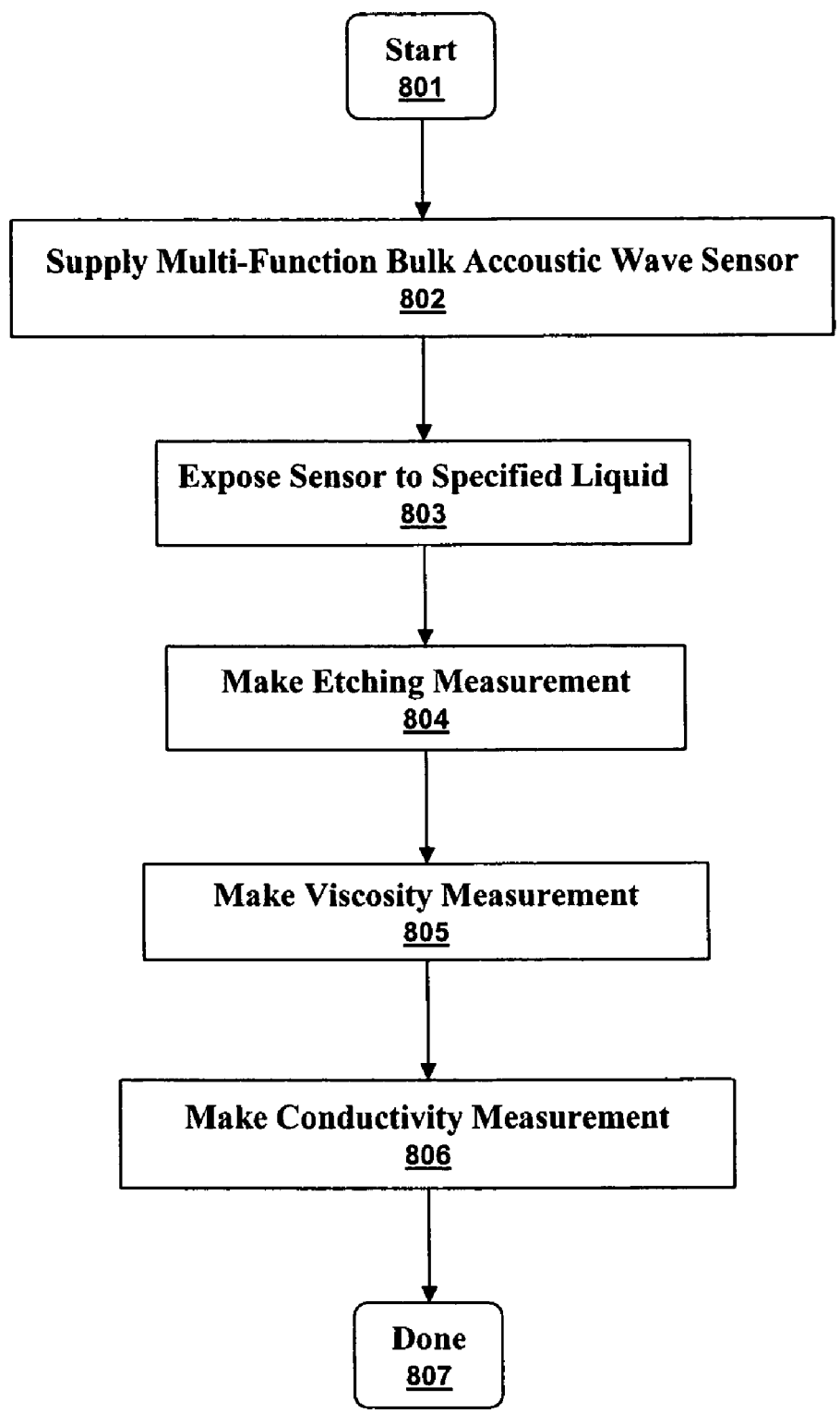
FIG. 8 illustrates a high level flow diagram of obtaining measurements of three physical properties with multifunction sensor in accordance with aspects of the embodiments.

FIG. 8 illustrates a high level flow diagram of obtaining measurements of three physical properties with multifunction sensor in accordance with aspects of the embodiments. After the start 801 a multifunction sensor is obtained 802 and exposed to a specified liquid 803, such as battery acid. Next, measurements of corrosivity 804, viscosity 805, and conductivity 806 are made before the process is done 807. Note that the measurements do not need to be performed in any particular order and that all three measurements can be made at the same time.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A system comprising:

a piezoelectric substrate having a front side and a back side;

a first conductor comprising a first contact on the back side and a front electrode on the front side wherein the front electrode comprises a material that is chemically reactive with a specified liquid;

a second conductor comprising a second contact on the back side and a back electrode on the back side;

a third conductor comprising a third contact on the back side and a runner on the front side; and a conductivity sensing element comprising a gap, the runner and the front electrode to thereby supply a sensor for obtaining a corrosivity measurement, a viscosity measurement, and a conductivity measurement of the specified liquid.

2. The system of claim 1 wherein the piezoelectric substrate is a quartz substrate.

3. The system of claim 2 wherein the quartz substrate is AT cut.

4. The system of claim 3 further comprising a housing arranged to protect the back side from the specified liquid.

5. The system of claim 2 wherein the quartz substrate is BT cut.

6. The system of claim 1 wherein the back electrode comprises a material that is chemically reactive with the specified liquid.

7. The system of claim 1 further comprising a housing arranged to protect the back side from the specified liquid.

8. A system comprising:
a piezoelectric substrate having a front side and a back side;
a first conductor comprising a first contact on the back side and a front electrode on the front side;
a reactive layer overlying the front electrode wherein the reactive layer comprises a material that is chemically reactive with a specified liquid;
a second conductor comprising a second contact on the back side and a back electrode on the back side;
a third conductor comprising a third contact on the back side and a runner on the front side; and
a conductivity sensing element comprising a gap, the runner and the front electrode to thereby supply a sensor for obtaining a corrosivity measurement, a viscosity measurement, and a conductivity measurement of the specified liquid.

9. The system of claim 8 wherein the piezoelectric substrate is a quartz substrate.

10. The system of claim 9 wherein the quartz substrate is AT cut.

11. The system of claim 10 further comprising a housing arranged to protect the back side from the specified liquid.

12. The system of claim 9 wherein the quartz substrate is BT cut.

13. The system of claim 8 further comprising a second reactive layer overlying the back electrode wherein the second reactive layer comprises a material that is chemically reactive with the specified liquid.

14. The system of claim 8 further comprising a housing arranged to protect the back side from the specified liquid.

15. A method comprising:
supplying a piezoelectric substrate comprising a front side and a back side wherein the piezoelectric substrate is patterned with a first conductor, a second conductor, and a third conductor wherein the first conductor comprises a first contact on the back side and a front electrode on the front side, wherein the second conductor comprises a second contact on the back side and a back electrode on the back side, wherein the third conductor comprises a third contact on the back side and a runner on the front side wherein a gap separates the runner and the front electrode and wherein the gap, the runner, and the front electrode are arranged to form a conductivity sensing element;
exposing the piezoelectric substrate to a specified liquid;
determining a fundamental frequency between the front electrode and the back electrode to obtain a corrosion measurement;
determining a vibration amplitude between the front electrode and the back electrode to obtain a viscosity measurement of the specified liquid; and
determining an electrical resistance across the gap to obtain a conductivity measurement of the specified liquid.

16. The method of claim 15 wherein the piezoelectric substrate is a quartz substrate.

17. The method of claim 16 wherein the quartz substrate is AT cut.

18. The method of claim 17 further comprising placing the quartz substrate in a housing arranged to protect the back side from the specified liquid.

19. The method of claim 16 wherein the quartz substrate is BT cut.

20. The method of claim 18 further comprising placing a reactive layer over the front electrode wherein the layer comprises a material that is chemically reactive with the specified liquid.

21. The method of claim 15 further comprising placing a reactive layer over the front electrode wherein the layer comprises a material that is chemically reactive with the specified liquid.

* * * * *